United States Patent
Itoh

(10) Patent No.: US 7,392,949 B2
(45) Date of Patent: Jul. 1, 2008

(54) TEST TUBE BARCODE READING APPARATUS

(75) Inventor: Teruaki Itoh, Kumamoto (JP)

(73) Assignee: IDS Co., Ltd.

( * ) Notice: Subject to any disclaimer, the term of this patent is extended or adjusted under 35 U.S.C. 154(b) by 499 days.

(21) Appl. No.: 11/097,373

(22) Filed: Apr. 4, 2005

(65) Prior Publication Data

US 2005/0252973 A1    Nov. 17, 2005

(30) Foreign Application Priority Data

Apr. 5, 2004    (JP) ............................... 2004-111064

(51) Int. Cl.
G06K 7/10 (2006.01)
G06K 15/00 (2006.01)
G01N 21/00 (2006.01)
G01N 31/00 (2006.01)
G01N 33/00 (2006.01)

(52) U.S. Cl. ............................. 235/462.01; 235/462.13; 422/63; 422/915

(58) Field of Classification Search ............ 235/462.13, 235/462.14, 462.43; 422/915
See application file for complete search history.

(56) References Cited

U.S. PATENT DOCUMENTS

| | | | | |
|---|---|---|---|---|
| 3,909,203 A | * | 9/1975 | Young et al. ................... | 422/67 |
| 5,286,959 A | * | 2/1994 | Demachi ................ | 235/462.14 |
| 5,455,006 A | * | 10/1995 | Aota et al. ..................... | 422/63 |
| 5,551,828 A | * | 9/1996 | Iles .............................. | 422/65 |
| 5,688,361 A | * | 11/1997 | Itoh ............................ | 156/362 |
| 6,081,326 A | * | 6/2000 | Rousseau et al. ............... | 422/65 |
| 6,257,091 B1 | * | 7/2001 | Cohen et al. ................... | 81/3.2 |
| 7,291,309 B2 | * | 11/2007 | Watson et al. ................. | 422/63 |
| 2007/0134131 A1 | * | 6/2007 | Watson et al. ................. | 422/65 |

FOREIGN PATENT DOCUMENTS

| | | |
|---|---|---|
| CN | 1111353 A | 11/1995 |
| EP | 0 639 774 A1 | 2/1995 |
| JP | 8-91487 | 4/1996 |
| JP | 8-104418 | 4/1996 |

* cited by examiner

*Primary Examiner*—Jared J Fureman
(74) *Attorney, Agent, or Firm*—Nixon & Vanderhye P.C.

(57) ABSTRACT

A barcode reading apparatus provided in a transfer mechanism to transfer intermittently a test tube holder holding a test tube with a barcode on periphery, comprises a barcode reader which reads a barcode of the test tube during halt of intermittent transfer by the transfer mechanism, and a rotating mechanism which holds sides of the test tube, and rotates the test tube to face the barcode to the barcode reader during the halt of intermittent transfer.

2 Claims, 6 Drawing Sheets

TEST TUBE BARCODE READING APPARATUS

CROSS-REFERENCE TO RELATED APPLICATIONS

This application is based upon and claims the benefit of priority from prior Japanese Patent Application No. 2004-111064, filed Apr. 5, 2004, the entire contents of which are incorporated herein by reference.

BACKGROUND OF THE INVENTION

1. Field of the Invention

The present invention relates to a barcode reading apparatus, which is provided in a test tube transfer path to transfer a test tube with a barcode label from a test tube rack to an inspection apparatus.

2. Description of the Related Art

A test tube containing a sample such as blood is labeled with a barcode indicating components of the sample, density and amount of a main component, etc. The barcode is read with a barcode reader provided in a test tube transfer path, and sent to an inspection apparatus or the like in a later stage as information for control or instruction in a subsequent process.

FIG. 1 and FIG. 2 show the side view and plane view of a conventional test tube barcode reader. A test tube holder 103 holds vertical a test tube 101 with a barcode label 102 in the upper periphery. The test tube holder 103 is held vertical and transferred by a transfer mechanism 105. The transfer mechanism 105 is provided with a barcode reader 109 at a barcode reading position to read the bar code 102 of the test tube 101. On the opposite side of the barcode reader 109 of the transfer mechanism 105, a test tube holder rotating mechanism 110 is provided to face the barcode 102 of the test tube 101 to the barcode reader 109 by pressing a roller to the outer periphery of the test tube holder 103 and rotating the test tube holder 103 in this state.

The test tube holder 103 comprises a cylinder 104 having a pair of flanges 104a and 104b on the lower periphery, and an annular groove 104c between the flanges. A leaf spring (not shown) is provided in the cylinder 104 to insert and hold the test tube 101 vertical.

The transfer mechanism 105 comprises a belt conveyer 106 which holds a number of test tube holders 103 vertical and conveys them intermittently at a regular intervals, and guide rollers 107 and 108 which have guide projections 107a and 108a to engage with the annular groove 104c of the test tube holder 103 with a play, and are provided on both sides of the belt conveyer 106.

The test tube holder rotating mechanism 110 comprises a pair of friction rollers 111 and 112 which are supported rotatably around the vertical axis of a guide rail 107 on one side of the rotating mechanism and pressed to one side of the periphery of the cylinder 104, an endless belt 113 which is wound around the pulleys of friction rollers 111 and 112 and rotates the friction rollers 111 and 112 together in the direction of the arrow in FIG. 2, and a drive motor 114 which drives and rotates the friction roller 111. The test tube holder rotating mechanism 110 is configured to read the barcode 102 of the test tube 101 faced to the bar code reader 109, by rotating the test tube 101 held by the test tube holder 103 by pressing the friction rollers 111 and 112 to the periphery of the holder cylinder 104 from one side and rotating the test tube holder in this state.

However, an idle clearance is formed in the engagement between the guide projections 107a/108a of the guide rails 107/108 and the annular groove 104c formed between the flanges of the test tube holder 103, as shown in FIG. 1. Thus, if the test tube holder 103 is rotated in the state that the friction rollers 111 and 112 are pressed to the periphery of the cylinder from one side, the test tube holder 103 and test tube 101 held thereby swing as indicated by a broken line in FIG. 1, or the flanges 104a and 104b of the test tube holder 103 are pressed strongly to the insides of the guide rails 107 and 108 or the guide projections 107a and 108a. In this state, the test tube holder 103 and test tube 101 held thereby cannot be rotated, and the barcode 102 cannot be faced exactly to the barcode reader 109. As a result, a problem of failing to read the barcode 2 occurs.

BRIEF SUMMARY OF THE INVENTION

The present invention has been made to solve the above problem. It is an object of the present invention is to provide a barcode reading apparatus, which can face a barcode of a test tube to a barcode reader and eliminates a problem of failing to read a barcode.

According to an embodiment of the present invention, there is provided a barcode reading apparatus provided in a transfer mechanism to transfer intermittently a test tube holder holding a test tube with a barcode label on the periphery, comprising a barcode reader which reads a barcode of a test tube during halt of intermittent transfer by the transfer mechanism, and a rotating mechanism which holds sides of the test tube, and rotates and faces the test tube to the barcode reader during the halt of intermittent transfer.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention and, together with the general description given above and the detailed description of the embodiments given below, serve to explain the principles of the present invention in which.

DETAILED DESCRIPTION OF THE INVENTION

Hereinafter, embodiments of a barcode reading apparatus according to the present invention will be explained with reference to the accompanying drawings.

Figure 1:
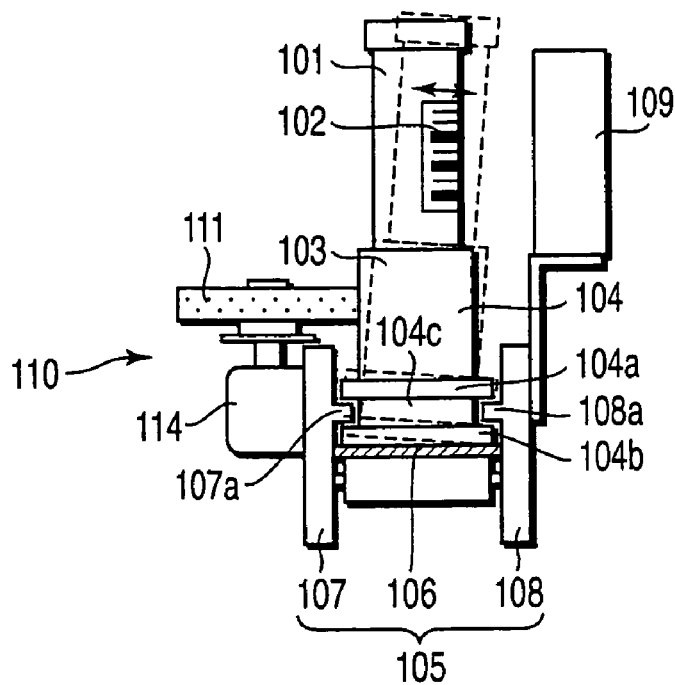
FIG. 1 is a longitudinal sectional view showing the structure of an essential part of a conventional barcode reading apparatus.
Figure 2:
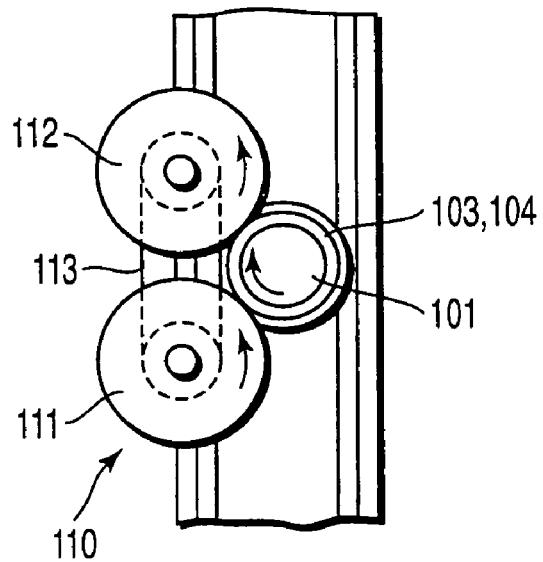
FIG. 2 is a transverse sectional view showing a friction roller part of FIG. 1.
Figure 3:
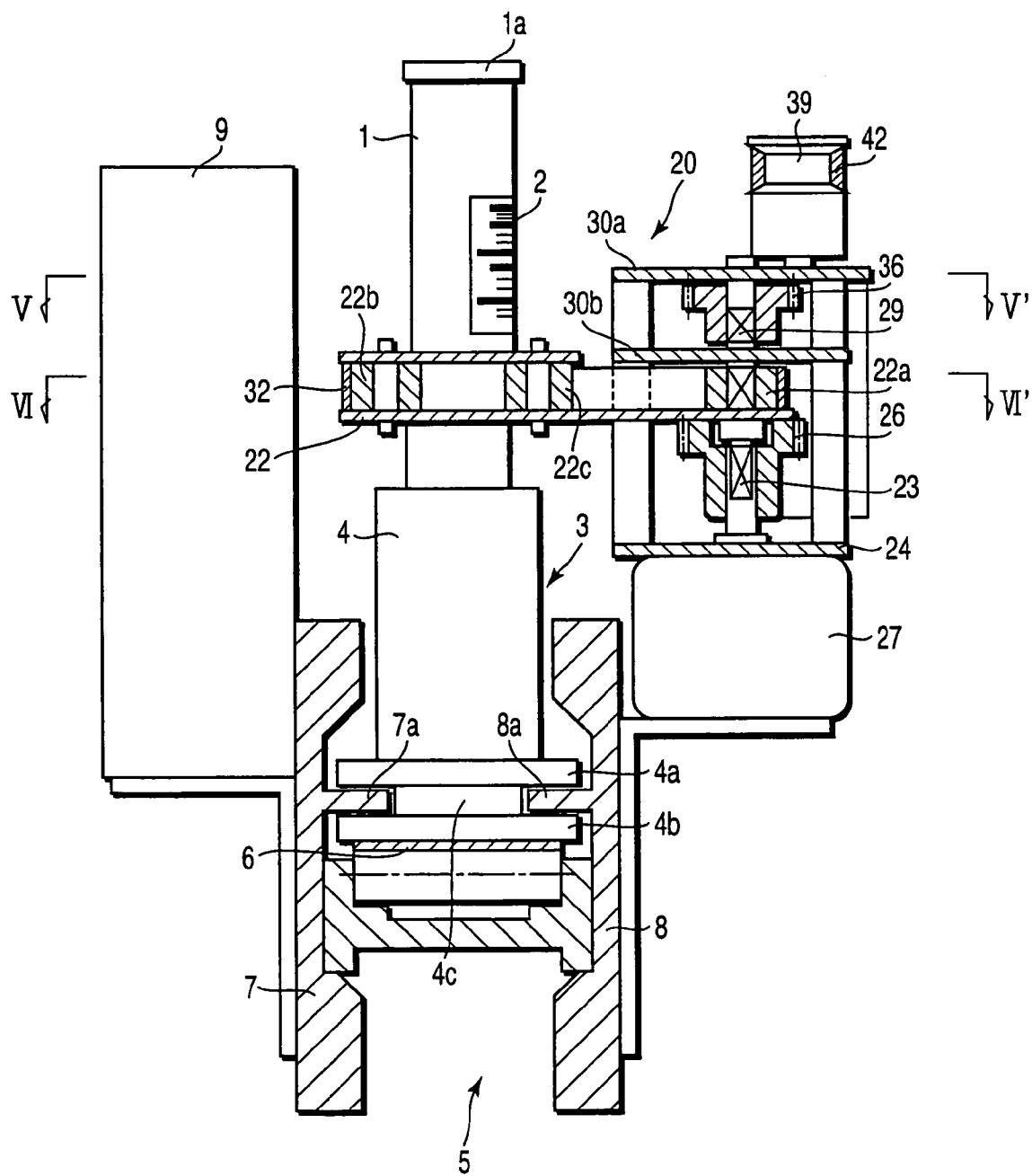
FIG. 3 is a longitudinal sectional view showing an essential part of a barcode reading apparatus according to a first embodiment of the present invention.
Figure 4:
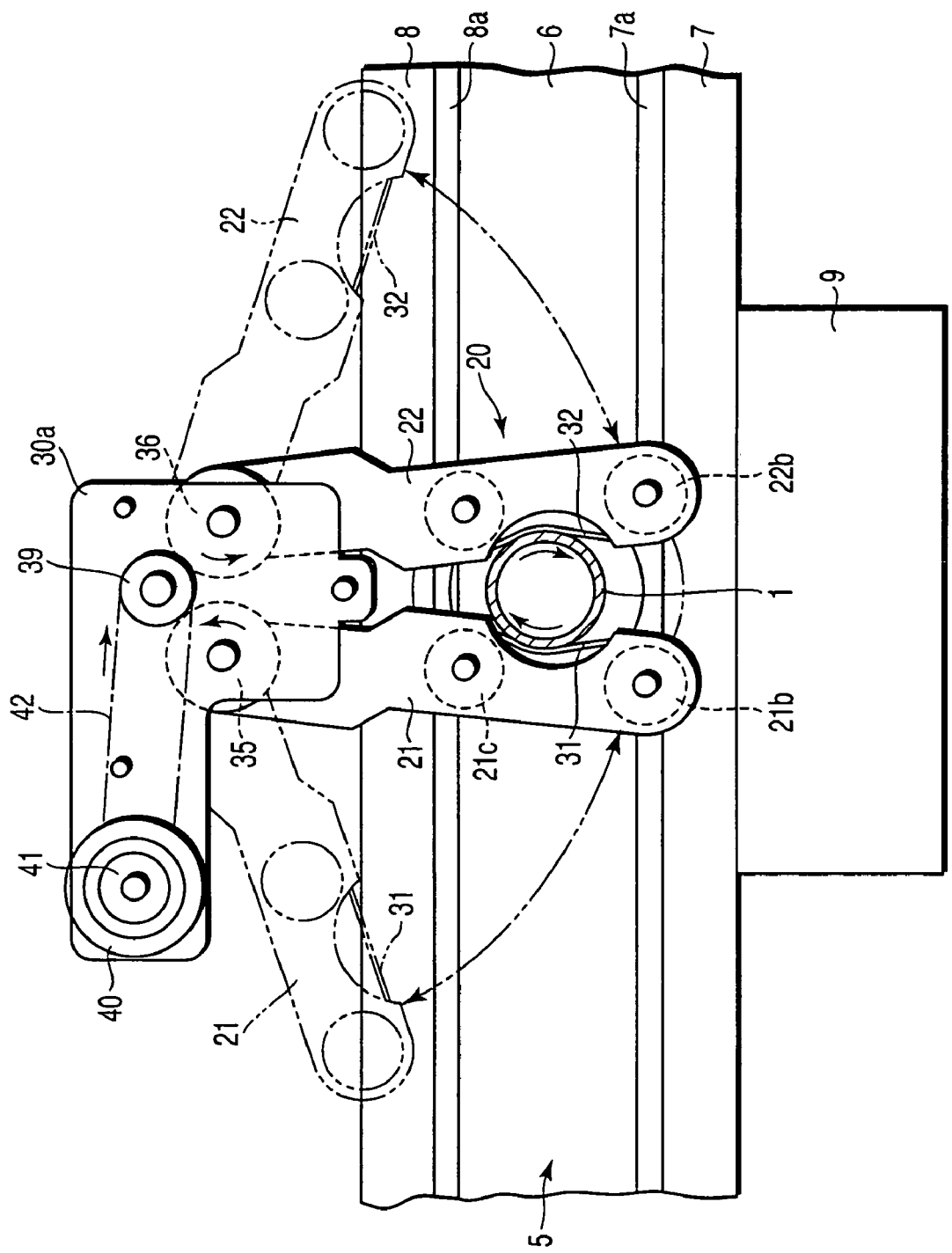
FIG. 4 is a plane view of the barcode reading apparatus shown in FIG. 3.
Figure 5:
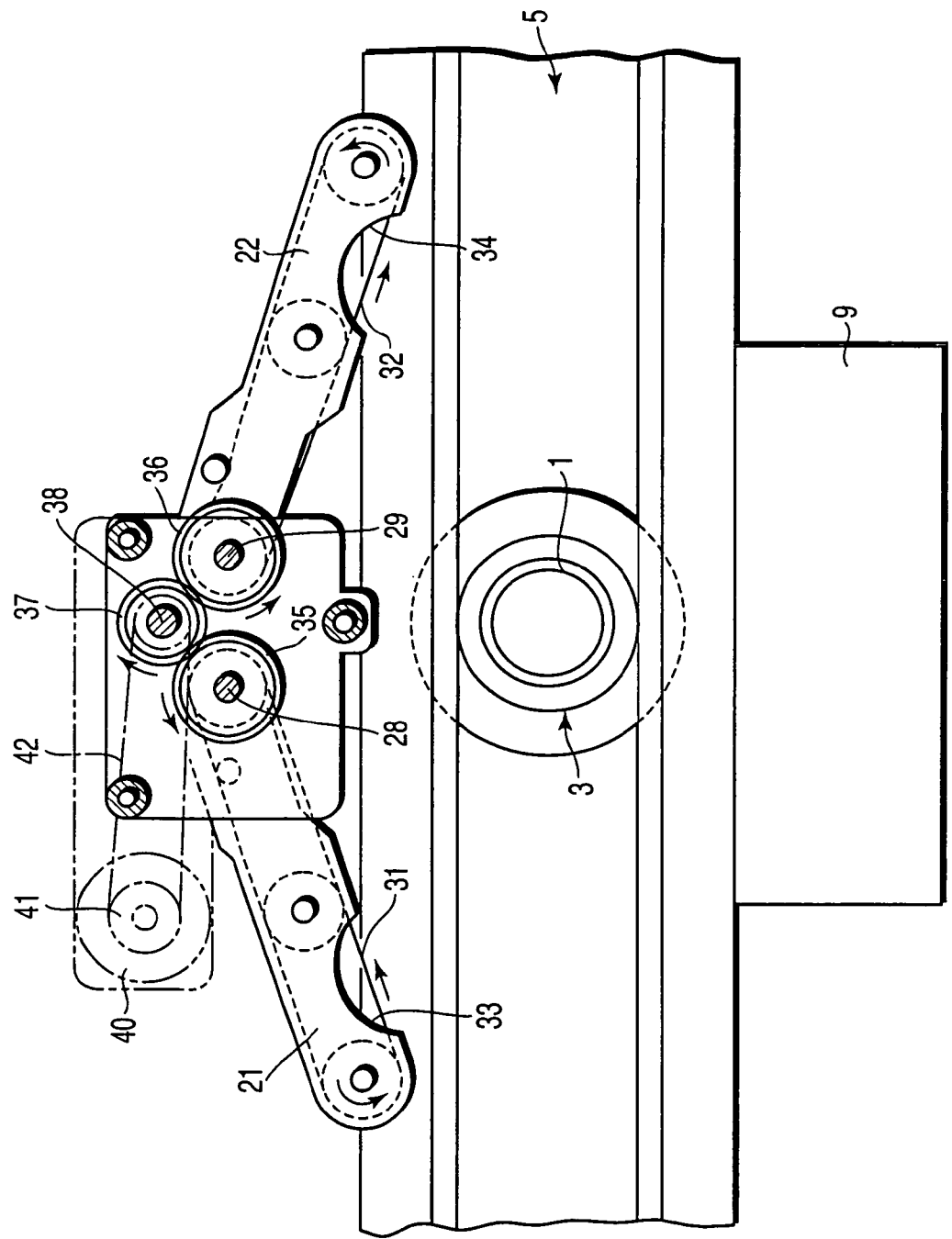
FIG. 5 is a transverse sectional view of a part taken along lines V-V' of FIG. 3 with an arm opened.
Figure 6:
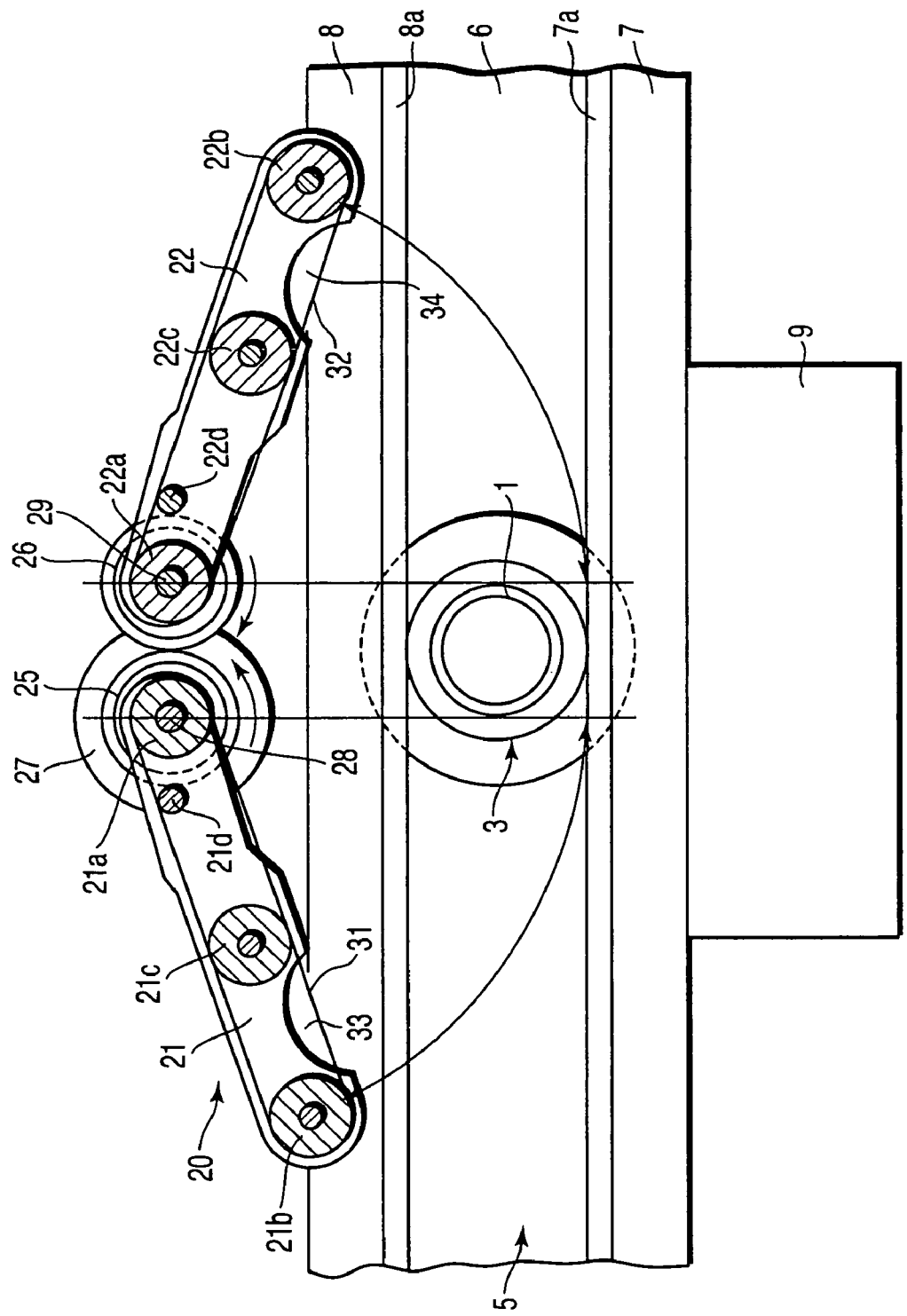
FIG. 6 is a transverse sectional view of a part taken along lines VI-VI' of FIG. 3 with an arm opened.

FIG. 3 is a longitudinal sectional view of an essential part of a barcode reading apparatus according to the first embodiment of the invention. FIG. 4 is a plane view of the barcode reading apparatus. FIG. 5 is a transverse sectional view of a part taken along lines V-V' of FIG. 3 with an arm opened. FIG. 6 is a transverse sectional view of a part taken along lines VI-VI' of FIG. 3 with an arm opened.

A test tube 1 has a barcode 2 on the upper periphery. The test tube 1 contains a sample such as blood, and the upper end opening is tightly closed with a plug 1a. A test tube holder 3 holds the test tube 1 vertical. The test tube holder 3 has a cylinder 4 having a pair of flanges 4a and 4b on the lower periphery, and an annular grove 4c between the flanges 4a and 4b. The cylinder 4 contains a leaf spring (not shown) to insert and hold the test tube 1 vertical.

A transfer mechanism 5 comprises a belt conveyer 6 which holds test tube holders 3 vertical and conveys them intermittently at regular intervals, and guide rails 7 and 8 which are provided on both sides of the belt conveyer 6 and has guide projections 7a and 8a to engage with the annular groove 4c of the test tube holder 3 with an idle clearance.

A barcode reader 9 provided at a barcode reading position of the transfer mechanism 5 reads the barcode 2 of the test tube 1. On the opposite side of the barcode reader 9 of the transfer mechanism 5, a test tube holder rotating mechanism 20 is provided to face the barcode 2 of the test tube 1 to the barcode reader 9 by rotating the test tube holder 3.

The test tube rotating mechanism 20 holds the side of the test tube 1 and rotates the test tube to face the barcode 2 to the barcode reader 9. The test tube rotating mechanism 20 has a pair of swing open-close arms 21 and 22, and a pair of rotary belts 31 and 32 laid over the arms 21 and 22. The test tube 1 is held by the rotary belts 31 and 32 as shown in FIG. 4, and given a rotating force by rotating the rotary belts 31 and 32.

The swing open-close arms 21 and 22 are configured as described below. Linked gears 25 and 26, which are engaged and synchronized with a proximal end axis 23 supported rotatably to a fixed support board 24, are provided to rotate together with the proximal end axis 23. The gears 25 and 26 are fixed to the arm proximal end. The proximal end axis 23 of one arm 21 is reversibly rotated with a rotary actuator 27. The arms 21 and 22 are moved to open and close by the motion of the linked gears 25 and 26, as indicated by a solid line and a dotted line in FIG. 4. The test tube holding parts of the arms 21 and 22 have arc-shaped notches 33 and 34 as a buffer where a part of the rotary belts 31 and 32 is exposed as shown in FIG. 4 to FIG. 6.

The rotary belts 31 and 32 are moved around drive pulleys 21a and 22a of the proximal end supported rotatably to the swing open/close arms 21 and 22, follower pulleys 21b and 22b of the distal end, intermediate pulleys 21c and 22c, and tension rollers 21d and 22d, as shown in FIG. 6.

Rotary drive axes 28 and 29 of the drive pulleys 21a and 22a are on the same vertical axis as the axis of the arm proximal end axis 23, and supported rotatably to unit boards 30a and 30b arranged and fixed above the fixed support board 24.

The rotary drive axes 28 and 29 are provided with a pair of linked gears 35 and 36, which are adjacent with certain intervals as shown in FIG. 5, and positioned between the unit boards 30a and 30b. An intermediate gear 37 which engages with the linked gears 35 and 36 as shown in FIG. 5, is attached rotatably to the unit boards 30a and 30b by a rotary axis 38.

An endless toothed belt 42 is wound around a toothed pulley 39 fixed to the upper end portion of the rotary axis 38 and a toothed pulley 41 fixed to a rotary axis of a servomotor 40 (mounted on the unit boards 30a and 30b), as shown in FIG. 4.

FIG. 3 and FIG. 4 show the state that the swing open/close arms 21 and 22 are closed, and the test tube 1 is held by the rotary belts 31 and 32 of the arms. When the toothed belt 42 is rotated by the servomotor 40 in the direction of the arrow with the test tube 1 held thereon, the intermediate gear 37 engages with the linked gears 35 and 36, the drive pulleys 21a and 22a are rotated, the rotary belts 31 and 32 are moved in different directions, the test tube 1 held on the belts 31 and 32 is turned at least once in the direction of the arrow, the barcode 2 of the test tube 1 is exactly faced to the barcode reader 9, and the barcode is read.

After the barcode reader 9 reads the barcode 2, the test tube rotating mechanism 20 stops rotation of the test tube 1. Then, a rotary actuator 27 is actuated, the linked gears 25 and 26 are engaged, the open/close arms 21 and 22 are synchronized and opened as indicated by an imaginary line (a chain double-dashed line) of FIG. 4, the test tube 1 is conveyed by the belt conveyer 6 to the next processing step, and a new test tube 1 is delivered to the barcode reading position.

As explained above, in the barcode reading apparatus of this embodiment, the test tube held by the test tube holder is held from both sides and rotated by the test tube rotating mechanism, and the barcode of the test tube is faced to the barcode reader. Therefore, the barcode can be exactly faced to the barcode reader, and the barcode can be read without fail.

Next, another embodiment of the present invention will be explained. The components corresponding to those of the first embodiment are given the same reference numerals, and detailed explanation will be omitted.

Embodiment 2

Figure 7:
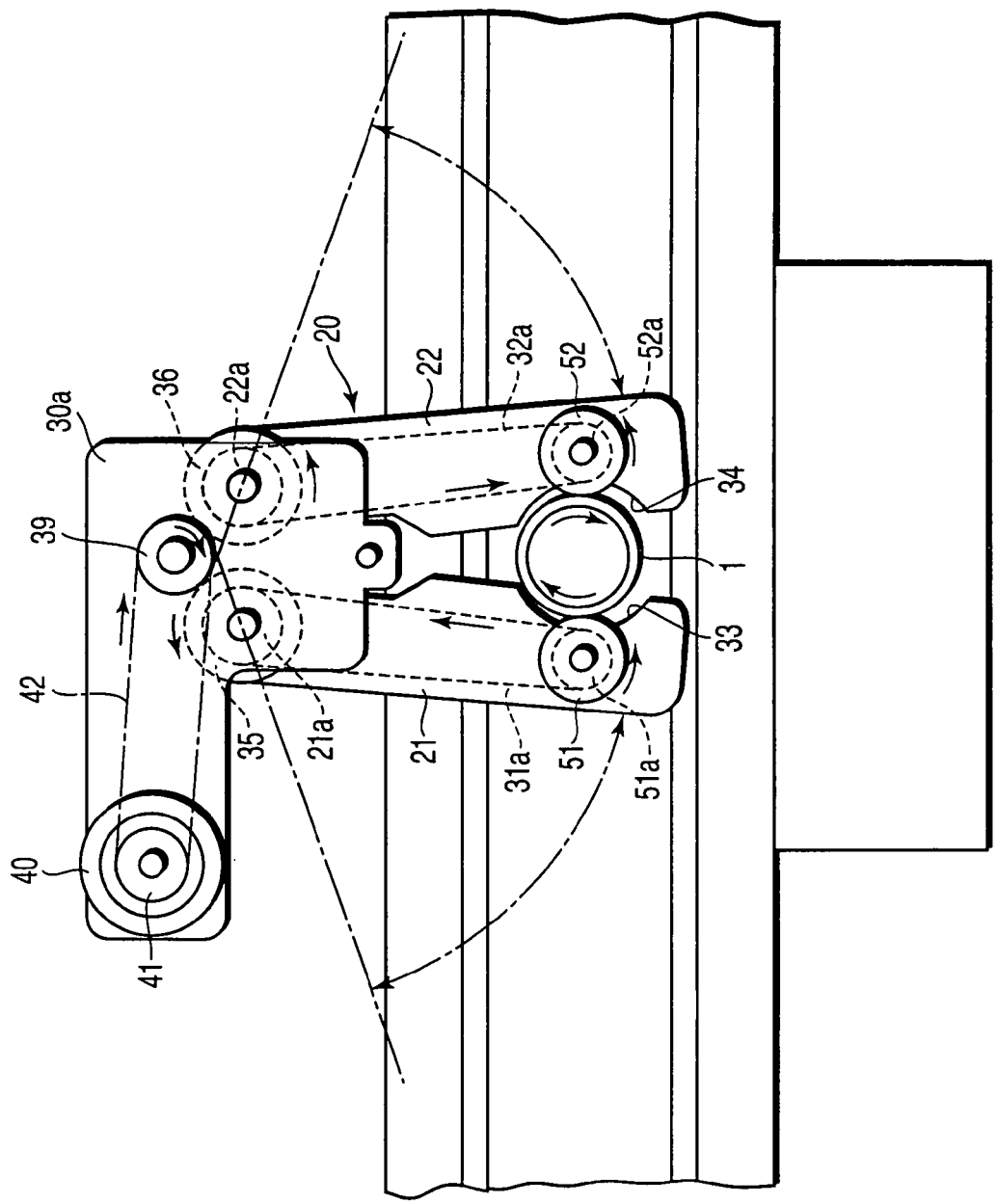
FIG. 7 is a plane view showing a barcode reading apparatus according to a second embodiment of the invention.

FIG. 7 shows a barcode reading apparatus according to a second embodiment of the invention. The second embodiment apparatus is different from the first embodiment in the following points. The test tube holder rotating mechanism 20 has a pair of swing open/close arms 21 and 22, and at least a pair of friction rollers 51 and 52 pivoted rotatably to a test tube holding part of the arms. The test tube 1 is held and given a rotating force by the friction rollers 51 and 52. The friction rollers 51 and 52 are driven and rotated in the direction of the arrow in the drawing by the linking of the endless belts 31a and 32a wound around the proximal end pulleys 21a and 22a of the arms 21 and 22 and the distal end pulleys 51a and 52a. The other configuration and functions are the same as the first embodiment. The same components are given the same reference numerals, and detailed description will be omitted.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A barcode reading apparatus provided in a transfer mechanism to transfer intermittently a test tube holder holding a test tube with a barcode on periphery, comprising:
 a barcode reader which reads a barcode of the test tube during halt of intermittent transfer by the transfer mechanism; and
 a rotating mechanism which holds sides of the test tube, and rotates the test tube to face the barcode to the barcode reader during the halt of intermittent transfer, wherein the rotating mechanism has a pair of open/close arms for holding the test tube, and a pair of rotary belts laid over the open/close arms for rotating the test tube.

2. The barcode reading apparatus according to claim 1, wherein the pair of open/close arms has linked gears to open the arms, which are engaged and synchronized with a proximal end axis of the arms.

* * * * *